United States Patent
Kleinert et al.

(10) Patent No.: US 8,955,384 B2
(45) Date of Patent: Feb. 17, 2015

(54) TEST PROBE AS WELL AS FAMILY OF TEST PROBES FOR THE NON-DESTRUCTIVE TESTING OF A WORKPIECE BY MEANS OF ULTRASONIC SOUND AND TESTING DEVICE

(75) Inventors: Wolf-Dietrich Kleinert, Bonn (DE); Gerhard Splitt, Cologne (DE)

(73) Assignee: GE Sensing & Inspection Technologies GmbH (DE)

( * ) Notice: Subject to any disclaimer, the term of this patent is extended or adjusted under 35 U.S.C. 154(b) by 471 days.

(21) Appl. No.: 13/319,615

(22) PCT Filed: May 12, 2010

(86) PCT No.: PCT/EP2010/056614
§ 371 (c)(1),
(2), (4) Date: Nov. 29, 2011

(87) PCT Pub. No.: WO2010/130819
PCT Pub. Date: Nov. 18, 2010

(65) Prior Publication Data
US 2012/0060612 A1    Mar. 15, 2012

(30) Foreign Application Priority Data
May 14, 2009  (DE) .......................... 10 2009 003 131

(51) Int. Cl.
*G01N 29/24*    (2006.01)
*G01N 29/26*    (2006.01)
*G01N 29/04*    (2006.01)

(52) U.S. Cl.
CPC .......... *G01N 29/2487* (2013.01); *G01N 29/262* (2013.01); *G01N 2291/056* (2013.01); *G01N 29/043* (2013.01)
USPC .............................................. 73/627; 73/632

(58) Field of Classification Search
USPC ..................... 73/627, 632, 599, 602
See application file for complete search history.

(56) References Cited

U.S. PATENT DOCUMENTS

| | | | |
|---|---|---|---|
| 4,195,530 A | 4/1980 | Ross | |
| 4,289,033 A * | 9/1981 | Prause et al. | ..................... 73/622 |

(Continued)

FOREIGN PATENT DOCUMENTS

| | | |
|---|---|---|
| DE | 102008037173 A1 | 7/2009 |
| DE | 102008002445 A1 | 10/2009 |

(Continued)

OTHER PUBLICATIONS

H. Krautkrämer "Detection and Classification of Defects", •Ultrasonic Testing of Material, 4th Edition, p. 313-319.

(Continued)

*Primary Examiner* — J M Saint Surin
(74) *Attorney, Agent, or Firm* — Cantor Colburn LLP (57) ABSTRACT

The invention relates to a test probe 10 for the non-destructive testing of a workpiece by means of ultrasonic sound. The test probe has an ultrasonic transducer 20 for the generation of an ultrasonic field, which is coupled acoustically to a delay line body 12, which is provided to be attached for a coupling of the ultrasonic field into the workpiece on a surface of the workpiece. Furthermore, the invention relates to a family of test probes as well as to a testing device for the non-destructive testing of a workpiece by means of ultrasonic sound, with a test probe 10, whose ultrasonic transducer 20 has a majority of independently controllable individual oscillators. Furthermore, a control unit 50 is provided, which is equipped to control the individual oscillators of the ultrasonic transducer 20 with phase accuracy in such a way, that a sound field rotationally symmetrical to the central beam is generated. The test probe or the family of test probes and the testing device are suitable in particular for the angular intromission of sound or for a utilization on curved workpiece surface areas.

20 Claims, 4 Drawing Sheets

(56) References Cited

U.S. PATENT DOCUMENTS

| | | | |
|---|---|---|---|
| 5,511,425 A | | 4/1996 | Kleinert |
| 5,583,292 A | * | 12/1996 | Karbach et al. ................. 73/638 |
| 6,186,947 B1 | * | 2/2001 | Ouchi ........................... 600/439 |
| 6,216,538 B1 | * | 4/2001 | Yasuda et al. ................ 73/570.5 |
| 7,757,558 B2 | * | 7/2010 | Bossi et al. .................... 73/609 |
| 8,596,127 B2 | * | 12/2013 | Falter et al. .................... 73/627 |

FOREIGN PATENT DOCUMENTS

| | | |
|---|---|---|
| DE | 102008002450 A1 | 10/2009 |
| EP | 1764614 A1 | 3/2007 |
| EP | 1995591 A2 | 11/2008 |
| EP | 2031385 A1 | 3/2009 |
| GB | 978183 | 12/1964 |
| JP | 58032158 A | 2/1983 |
| WO | 2004065594 A2 | 8/2004 |

OTHER PUBLICATIONS

International Search Report PCT/EP2010/056614; Dated Jan. 17, 2011.

H. Krautkrämer "Detection and Classification of Defects", •Ultrasonic Testing of Material, 4th Edition, p. 313-319, (1990).

* cited by examiner

Fig. 6 ated States Patent US 8,955,384 B2

TEST PROBE AS WELL AS FAMILY OF TEST PROBES FOR THE NON-DESTRUCTIVE TESTING OF A WORKPIECE BY MEANS OF ULTRASONIC SOUND AND TESTING DEVICE

TECHNICAL FIELD

The present invention relates to a test probe for the non-destructive testing of a workpiece by means of ultrasonic sound, to a testing device for the non-destructive testing of a workpiece by means of ultrasonic sound, to a family of test probes for the non-destructive testing of a workpiece by means of ultrasonic sound and to a utilization of a test probe or a family of test probes according to the present invention. The invention relates in particular to an angular intromission of sound in the case of curved workpiece surface areas. In the context of the present application, an object to be tested is designated for the sake of simplicity as "workpiece" or as "unit under test."

In particular, the present invention relates to the area of ultrasonic testing in the framework of the so-called DGS-method.

BACKGROUND

The DGS-method (DGS=Distance, Gain, Size) has been known for a long time from the prior art. The DGS-method has been originally developed for plane circular straight beam probes generating a rotational symmetric sound field in the test material. It is based on the comparison of the echo amplitude of a real reflector in a workpiece (for example, of an inclusion, a cavity, a crack, etc.) with echo signals of circular disk reflectors. With the aid of a so-called DGS-diagram, an inspector can determine a equivalent reflector size (ERS) characterizing the real reflector through the comparison of the echo amplitude of a real reflector with an array of curves of circular disk reflectors recorded in the DGS-diagram. For this he selects the device gain, so that a reference echo (as a rule a back wall echo) attains a pre-set screen height. Also, the reflector echo is adjusted by means of the gain adjustment to the same screen height. The gain difference between reference and reflector echo, as well as the sound paths go into the DGS-evaluation. Often the DGS-method is used for sizing reflectors in the workpiece, which, for example, exceed recording limits pre-set by technical standards (see for example EN 583-2). Further details regarding the non-destructive testing of a workpiece by means of ultrasonic sound, in particular by means of the DGS-method, can be learned from the book J. Krautkrämer, H. Krautkrämer, *Materials Testing with Ultrasonic Sound,* 1986 (5$^{th}$ edition), released in the Springer Publishing House (ISBN 3-540-15754-9), here particularly Chapter 19.2.

However, in the case of recent experimental studies by means of the DGS-method, it was found that with measurements in angular intromission of sound or of an intromission of sound in the case of curved workpiece surface areas, unexpectedly large deviations resulted from the values, which had been expected for the circular disk reflectors examined. The size of the deviation depended thereby on the type of test probe utilized.

BRIEF SUMMARY

The present invention has thus made it its task to specify a test probe for the non-destructive materials testing by means of ultrasonic sound particularly in angular intromission of sound or in the case of an intromission of sound on a curved workpiece surface area, which is shaped so that the sound field formed in the workpiece permits an especially simple interpretation or evaluation of echo signals. Furthermore, a testing device with a test probe and a control unit should be specified, which permits the realization of the same advantages. Finally, a family of test probes should be specified, whose sound field in a workpiece in turn permits a simplified interpretability or evaluability. Finally, an advantageous application of a test probe or family of test probes according to the present invention or a testing device according to the present invention should be specified.

In the case of an intromission of sound into a workpiece with a plane surface area, the solution of this task is based on the proposal to transfer the sound field of a pre-set perpendicular test probe with a plane circular ultrasonic transducer and known delay line mathematically to an angular intromitting transducer with pre-set delay line and intromission angle, which forms in the testing material the same sound field under the selected intromission angle as the pre-set perpendicular test probe.

On the other hand, if an intromission of sound into a workpiece with non-planar surface area is examined, then the solution of the task is based on the proposal to transfer the sound field of the pre-set perpendicular test probe with plane circular ultrasonic transducer and known delay line in the case of intromission of sound into a planar surface area mathematically to a likewise perpendicular intromitting transducer with pre-set delay line, in which the design of the coupling surface area of the delay line body, i.e., the area, which is in contact with the workpiece, to which the non-planar surface area of the workpiece is adjusted. Here, a cylindrically curved work-piece surface area is mentioned in an exemplary manner. Thereby, the latter transducer should form the same sound field in the testing material under the selected sound intromission conditions of the non-planar surface area of the workpiece as the pre-set perpendicular test probe in the case of sound intromission into a planar surface area.

In the case of the delay line it can also be a matter of water, i.e., the test probe is used in the so-called immersion technique method.

Finally, based on the same considerations, the examination of the general case of an angular intromission of sound across a non-planar surface of the workpiece is also possible.

A test probe according to the present invention is provided for the non-destructive testing of a workpiece by means of ultrasonic sound in angular intromission of sound. It has an ultrasonic transducer for the generation of an ultrasonic field, which is coupled acoustically to a delay line body. The delay line body on its part is provided for a coupling of the ultrasonic field to be fitted into the workpiece with a coupling area on a surface area of the workpiece. This surface area can be planar, but it can also be curved. As a rule, the coupling surface area of the delay line body is designed in a manner complementary to the geometry of the workpiece to be examined.

In the context of the complex theoretical and experimental studies, it has now been shown that the interpretability of ultrasonic signals, which originate from reflectors in the volume of the workpiece, can be considerably improved, if it is ensured through appropriate technical measures, that the ultrasonic field generated by the test probe after the coupling into the workpiece is essentially rotationally symmetrical with reference to its main direction of propagation. An actual rotational symmetry is particularly preferable here. However, in the context of the present invention under "rotationally symmetrical", a sound field should also be understood, which has a rotational symmetry with regard to the main direction of propagation, i.e., can be transformed into itself by a rotation around the main direction of propagation at, for example, 120° (threefold symmetry), 90° (fourfold symmetry) or also 60° (sixfold symmetry).

According to the present invention, that surface area of the delay line body, at which the ultrasonic transducer is located, is not shaped in a planar manner. In particular, the design of the surface area of the delay line body, at which the ultrasonic transducer is located, can be selected so that elementary waves, which emanate from different points of the ultrasonic transducer, despite angular intromission or intromission across a non-planar work-piece surface area in the volume of the workpiece behave as in the case of the pre-set perpendicular test probe with circular oscillator, i.e., in the workpiece form the same sound field rotationallty symmetrical to the central beam.

This problem can be solved by transferring the time of flight for all sound beams from a flat circular straight beam probe to an angle beam probe with a given delay line length and a given intromission angle under consideration of Fermat's principle and the refrectaion at the interface between delay line and test material. This calculation is carried out for all possible sound beams within the nearfield. The nearfield of the plane circular transducer is characterized by the fact that the difference in time of flight between the central beam and the beams from the perimeter of the circular transducer is T/2, in which T is the cycle duration of the ultrasonic sound. By doing this the resulting point cloud defines the shape of the new transducer for the angle beam probe.

It has to be mentioned that above specified condition is exactly true only in case of continuous ultrasound waves. Within most test settings though pulsed ultrasound waves are used. As experimental finding we can report that use of pulsed ultrasound within the context of the present invention seems to result in a minor deviation from above specified condition classical near-field condition. This deviation can be correlated with the high dispersity of short ultrasound pulses and can be accounted for by introducing a correction factor A which is of empirical nature. Typically A is in the range of 0.8 and 1. Hence to improve the overall accuracy of the method according to the present invention one would either introduce a proportional correction factor A for each given test probe which has to be determined experimentally. Alternatively, instead of relying on the classical near-field length condition a novel starting point for the evaluation of the pulsed sound field as described in further detail in the preceding paragraphs is determined which differs from above mentioned classical near-field condition. It has been found that numerical simulation of the acoustic field of a given test probe operated in pulsed-mode allows for a rather precise determination of the location of the last maximum of the sound pressure on the acoustical axis. This location is then identified as numerical near-field length and accounts for the specific nature of pulsed ultrasound waves. While the first approach is advantageous due to its simplicity the latter leads to superior results in the practical application of the method and the probe according to the present invention.

It has become apparent that a test probe according to the present invention is particularly suited to the determination of the size of a reflector in a workpiece by means of the DGS-method under a given intromission angle and/or in the case of an intromission of sound across a non-planar surface area of the workpiece.

Various technical concepts are discussed below, with which a sound field distribution according to the present invention of the ultrasonic field generated by the test probe can be generated after its complete entrance into the volume of the workpiece.

In most applications, it has proved to be advantageous, if the surface area of the delay line body, at which the ultrasonic transducer is located, has an S-shaped contour in the sound intromission plane. Thereby, that plane is referred to as a sound intromission plane, which is fixed by the main direction of propagation of the ultrasonic sound in the delay line body and the surface normal on the workpiece surface area at the coupling location of the ultrasonic sound. The coupling location is given by the point, at which the acoustic axis cuts the bounding surface between delay line body and workpiece.

On the other hand, perpendicular to the intromission plane it has proved to be advantageous, if the surface area of the delay line body, at which the ultrasonic transducer is located, is described by a function, which has an absolute minimum in the intromission plane. In particular, this function can correspond essentially to a parabola opened upwards. In the context of this application this should mean, that it is a matter of a function, which possesses an absolute minimum, which lies in the intromission plane, and as a rule is opened upwards. Often in the vicinity of the intromission plane, the function can be well approximated by a parabolic function, also, if necessary, by a polynomial of a higher (even=$4^{th}$, $6^{th}$, etc.) order.

As explained previously, it has proved to be advantageous, if the ultrasonic field, which is formed in the workpiece, is rotationally symmetrical to the main direction of propagation in the workpiece. In particular, this means, that the beam cross-section in the workpiece is circular. Nevertheless, it has proved to be advantageous, if the ultrasonic transducer in an angle beam probe, which is used for the generation of the ultrasonic field, is not circular, i.e., has no circular circumferential line. Rather it has proved to be favorable, if the circumferential line of the ultrasonic transducer in general has no rotational symmetry, in particular is not circular or has the form of a regular polygon.

Based on the acceptance of an ultrasonic field in the workpiece, which is rotationally symmetrical to the central beam, which on its part is inclined towards the surface normal of the workpiece surface area at the coupling location, it is possible, with the application of Fermat's principle to the sound beams, to determine the optimal form and the optimal circumferential line of a corresponding ultrasonic transducer, which is applied to an area of the delay line body, whose surface normal is inclined towards the surface normal of the workpiece surface area at the coupling location. In the practice of ultrasonic testing, typical intromission angles are 25° to 75°, particularly 45°, 60° and 70°. The required angles of inclination arise here through the application of the law of refraction depending on the original material. The data of an ultrasonic field in the workpiece can be obtained, for example, from the calculation of an ultrasonic field of a typical test probe for the perpendicular intromission with a circular plane transducer. For simplification in the case of sound field calculation of this reference test probe, a delay line body is dispensed with. Based on the calculated sound field of the reference test probe, one now examines an angular intromitting test probe with delay line body, in which the ultrasonic transducer is located on a surface area of the delay line body, for example, glued on. Furthermore, one stipulates that in the workpiece the sound field of the angular intromitting test probe should be in accordance with the sound field of the perpendicular intromitting reference test probe, i.e., in the workpiece rotational symmetry should exist with regard to the main direction of propagation as well as at the end of the near field the last sound pressure maximum in the main direction of propagation. Under the mentioned boundary conditions, the deviation can be determined of the ultrasonic transducer of the angular intromitting test probe from the plane configuration of the transducer of the reference test probe. As a result, one obtains the geometry of the no longer plane area of the delay line body, to which the ultrasonic transducer should be attached.

One obtains a second improvement of the accuracy, if in addition the angular dependence of the delay line body—workpiece coupling factor is considered, which is tabulated for many material combinations.

Finally, the—often perceptible—sound attenuation in the delay line body can still be considered, which due to the different routes of the several elementary waves in the delay line body leads to a further deformation of the sound lobe transmitted by the ultrasonic transducer. Also, this can be considered by way of calculation.

From the examination of the perimeter beams of the ultrasonic field accepted as rotationally symmetrical in the workpiece, the precise form of the circumferential line of a real ultrasonic transducer can additionally be determined in the described manner.

Altogether, from this calculation, which requires as input parameters in general the frequency of the ultrasonic transducer, the sound velocities in the delay line body and in the workpiece, the delay lines of perpendicular and angular test probe, the diameter of the circular transducer of the perpendicular test probe and the intromission angle, one obtains the spatially resolved deviation of the corresponding (two-dimensional, but extending into three dimensions) ultrasonic transducer from a surface area of the delay line body accepted as planar, to which the ultrasonic transducer is/should be applied and the circumferential line of the corresponding transducer, whose ultrasonic field after its coupling into the workpiece in the case of the pre-set angular intromission in the workpiece is rotationally symmetrical to the main direction of propagation within the test material.

The aforementioned process steps thus permit it to determine a corrected design of the area of the delay line body, to which the ultrasonic transducer is acoustically coupled ("transducer surface"), for example, by adhesive bonding. Furthermore, a concrete form of the circumferential line of the corresponding ultrasonic transducer can be determined. These results can be immediately used, for example, to cut out an ultrasonic transducer with adjusted design, i.e., circumferential line, from a planar plate or film of a piezoelectric or composite material, which is suitable for the production of an ultrasonic transducer. Through corresponding finish-machining of the transducer surface of the delay line body, to which the ultrasonic transducer is acoustically coupled, for example, by CNC-machining, the required deviation of the corresponding ultrasonic transducer from the planar configuration can then be achieved. It has proved reasonable, to determine a specific corresponding transducer configuration (circumferential line, deviation from a planar configuration) for a pre-set geometry of the delay line body, a pre-set ultrasonic transducer frequency as well as a pre-set material of the workpiece as well as of the delay line body. However, this is not a mandatory requirement, if less demanding requirements in the accuracy of the measurement are set. A concrete example will be discussed subsequently in the context of the execution example.

Up to now it has been assumed, that in the case of the ultrasonic transducer used it is a matter of a one-piece individual oscillator. But alternatively the ultrasonic transducer can also have a majority of independently controllable individual oscillators. In particular, such a test probe can be shaped, so that the rotational symmetry according to the present invention can exist in the workpiece, when the individual oscillators, for example, are controlled in-phase by a separately designed control unit. In such a configuration, the surface area of the delay line body, to which the ultrasonic transducer is coupled, will in turn not be a planar area, as previously described.

In the framework of extensive studies it has become apparent, moreover, that independent of the form of the transducer surface, comparable advantages can be realized, if the ultrasonic transducer of the test probe has a majority of independently controllable individual oscillators. If one combines a test probe, which has such a segmented ultrasonic transducer, with a control unit, which is equipped to control the individual oscillators of the phase-accurate ultrasonic transducer in such a way that the ultrasonic field generated by the test probe after the coupling into the workpiece is essentially rotationally symmetrical to the central beam, then with such a testing device the advantages according to the present invention can in turn be realized. The previously described deviation of the corresponding two-dimensional ultrasonic transducer from a planar configuration can, for example, also be realized by an equivalent phase-accurate control of the individual oscillators of the ultrasonic transducer. The prerequisite for this is only a sufficient time resolution power of the control unit of the testing device. As a rule, however, the phase-accurate control of the individual oscillators of the ultrasonic transducer does not replace the previously described adjustment of the circumferential line of the ultrasonic transducer. In most cases, this is additionally required for the achievement of a rotationally symmetrical beam profile in the workpiece.

Furthermore, in a preferred further development the control unit of a testing device according to the present invention is equipped to control the individual oscillators of the ultrasonic transducer with phase accuracy in such a manner, that the main direction of the propagation of the ultrasonic field generated by the test probe, i.e., the direction of the central beam, can be varied at least in a plane, for example, the plane of incidence. This typical characteristic of a so-called "phased array," as it is well-known from the prior art, can also be realized with a testing device according to the present invention. As a rule, the test probe of such a testing device is formed in such a manner, that in the case of in-phase control of the individual oscillators in the workpiece, a rotationally symmetrical sound field is formed, whose main direction of propagation is inclined towards the surface normal at the coupling point (=angular intromission). But this is not mandatorily the case, also a phase-accurate (delayed against each other) control of the individual oscillators can be required for an angular intromission under the desired/pre-set intromission angle. A modification of this intromission angle is then possible by means of known phase control of the individual oscillators.

In a preferred further development of the testing device according to the present invention, the individual oscillators are arranged in the form of a two-dimensional array. This permits it to shape the surface area of the delay line body, at which the ultrasonic transducer is located, in a planar manner, and to realize the required adjustments for the generation of an ultrasonic beam, which is rotationally symmetrical in the workpiece to the main direction of propagation, exclusively through a phase-accurate control of the individual oscillators of the 2d-array. This phase-accurate control of the individual oscillators will thereby in general be specific for the selected intromission angle.

In an alternatively preferred embodiment of the testing device according to the present invention, the individual oscillators of the ultrasonic transducer are arranged in the form of a linear array. The longitudinal axis of the linear array is thereby preferably arranged in the intromission plane.

In an advantageous first embodiment of this execution example, the surface area of the delay line body, at which the ultrasonic transducer is located, is shaped in the direction of the longitudinal axis of the linear array in a planar manner. For the generation of a rotationally symmetrical beam profile in the workpiece, the individual oscillators of the array are then controlled in an individually phase-accurate manner specific for the selected intromission angle.

In a second advantageous embodiment, the surface area of the delay line body, at which the ultrasonic transducer is located, is shaped in the direction of the longitudinal axis of the linear array deviating from the planar configuration, as previously already described. This permits it to achieve the desired rotationally symmetrical beam profile in the workpiece for a pre-set angle of incidence at least in the plane of incidence also in the case of in-phase control of the individual oscillators.

For the achievement of an optimal result with regard to the desired rotational symmetry in the workpiece, the form of the area of the delay line body deviating from the plane, at which the ultrasonic transducer is located, is calculated perpendicular to the intromission plane as previously described and is realized through suitable design/materials processing of the delay line body. Since also the design of the surface area of the delay line body depends on the actual intromission angle, the design of the delay line body is advantageously optimized, so that in the case of a pre-set intromission angle, a rotationally symmetrical beam profile results. This pre-set intromission angle can be given, for example, directly by an in-phase control of all individual oscillators of the linear array.

If in this configuration, the intromission angle is electronically modified, for example, by corresponding phase-accurate control of the individual oscillators of the array, then basically the design of the transducer surface of the delay line body bearing the array would have to be optimized again for this altered angle. But here it has been surprisingly shown, that the deviations of the beam profile occurring in the workpiece from the desired rotational symmetry are so minor, that an optimization of the area profile perpendicular to the intromission plane for a (unique) central intromission angle leads in practice as a rule to satisfactory results. The change of the shape of the transducer by different steering angles can be adopted by calculating the delay laws accordingly.

As previously already explained, as a rule both the delay line body-workpiece coupling factor as well as the sound attenuation in the delay line body (due to the varying run lengths in the delay line body) are dependent upon the intromission angle. This influence can be compensated simply in the case of a phased-array-test probe, as the transmit amplitude or/and the reception amplitude of the individual oscillators of the array are individually adjusted.

Furthermore, a family of test probes of equal frequency for the non-destructive testing of a workpiece by means of ultrasonic sound has proved to be advantageous, which includes a first test probe, which is provided for the intromission of sound under a first intromission angle, and a second test probe, which is provided for the intromission of sound under a second intromission angle, and a third test probe, which is provided for the intromission of sound under a third intromission angle (typical angles are, for example, 45°, 60° and) 70°. The family of test probes is characterized in that in the near field of all test probes in the workpiece, the ultrasonic field generated by a test probe in the direction of the central beam is essentially in accordance with the ultrasonic field generated by the other test probes in the direction of its central beam. Preferably all test probes are thereby provided for the angular intromission of sound. In particular, all test probes correspond preferably to a test probe according to the present invention in accordance with one or more of the previously described preferred embodiments. Such a family of test probes is especially suitable for the determination of the size of a defect in a workpiece by means of the DGS-method under several intromission angles.

An especially simple application of the test probes of the family of test probes results, if the length of the sound paths in the test material in the main direction of propagation up to the near-field end is essentially in agreement in the case of all test probes.

BRIEF DESCRIPTION OF THE DRAWINGS

Further advantages and characteristics arise from the subsidiary claims as well as the execution examples, which are elucidated in detail below on the basis of the drawing. In the latter

DETAILED DESCRIPTION

Figure 1:
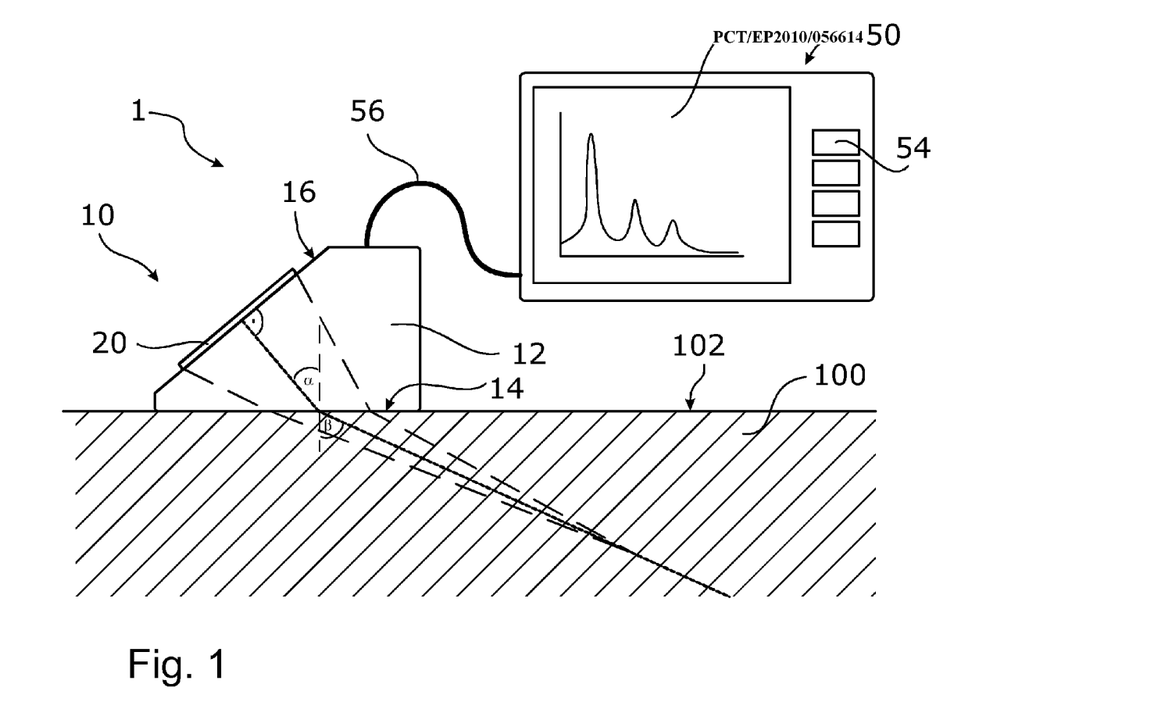
FIG. 1: shows a schematic diagram of a test set-up according to the present invention.

A test set-up 1 according to the present invention includes a test probe 10, which on its part includes a delay line body 12, which can be produced, for example, from Plexiglas®. In the test set-up shown, in the case of test probe 10 it is a matter of an angular test probe, which is provided to generate an ultrasonic beam in a workpiece 100, which is inclined at an angle β towards the normal of the entrance surface. Thereby, the delay line body 12 has a coupling surface area 14, with which the delay line body 12 of the test probe 10 is attached to the surface area 102 of the workpiece 100. As a rule, the coupling surface area 14 of the test probe 10 is adjusted in its geometry to the geometry of the workpiece surface area 102, as this is known from the prior art.

A suitable ultrasonic transducer 20 is located at a transducer surface 16 of the delay line body 12, in such a way, that a good acoustical coupling of the ultrasonic transducer 20 to the delay line body 12 results. The ultrasonic transducer 20 can, for example, consist of a piezoceramic and be glued onto the transducer surface 16. The transducer surface 16 is as a rule inclined at an angle α towards the surface normal of the work-piece surface area 102. The ultrasonic transducer 20 is controlled by means of a separately designed control unit, with which the latter is connected via a control line 56. As a rule, the control unit 50 includes a display 52 for the graphic depiction of the recorded echo signals and if necessary of the device adjustments, which in part can be adjusted via a majority of operational controls 54. The control unit 50 is thereby configured in pulse-echo technique for the control of the test probe 10. In particular, the control unit 50 can be provided to determine the size of a reflector in the workpiece 100 according to the so-called DGS-method and if necessary to plot it for the operator on the display 52. Special advantages arise in this connection, if the control unit 50 corresponds to the specifications in the German patent applications DE 10 2008 037 173, DE 10 2008 002 445 or DE 10 2008 002 450 as well as in U.S. Pat. No. 5,511,425 of the holder of the present application. The subject matter of the patent applications referred to is added completely to the scope of disclosure of the present application by this reference.

Figure 2:
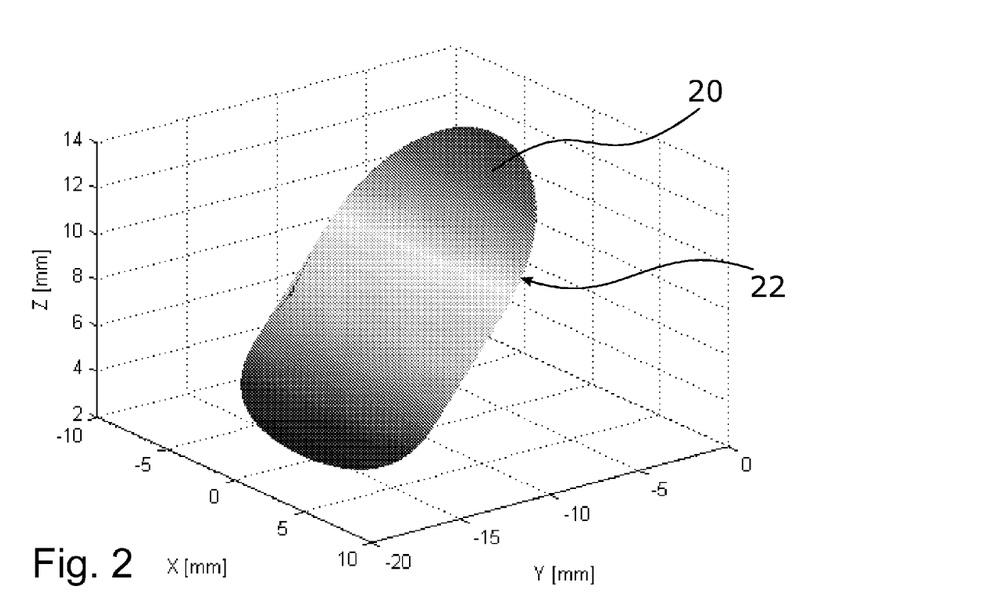
FIG. 2: shows a three-dimensional depiction of an ultrasonic transducer of a test probe according to the present invention, from which the deviation of the circumferential line of the ultrasonic transducer from the hitherto accepted circular or rectangular configuration becomes clear.

FIG. 2 now shows a three-dimensional depiction of an ultrasonic transducer 20 optimized according to the present invention, from which the deviation of the circumferential line 22 of the ultrasonic transducer 20 from the circular or rectangular form already known from the prior art as optimal becomes clear. On the basis of the required rotationally symmetrical beam profile in the workpiece, a clearly larger extension of the ultrasonic transducer 20 in the intromission plane results than perpendicular thereto. Furthermore, a circumferential line 22 symmetrical indeed to the plane of incidence arises, which is, however, not point-symmetrical with regard to the transducer point X or with regard to a plane running through this point perpendicular to the plane of incidence. The optimization was carried out for values close to reality, namely for a delay line of 13.40 millimeters, a diameter of the perpendicular intromitting circular ultrasonic transducer 20 serving as the starting point of the calculation of 13.00 millimeters, an intromission angle of 60°, an ultrasonic frequency of 2 MHz, a sound velocity in the delay line body of 2.730 mm/microsecond as well as a sound velocity in the workpiece of 3.255 mm/microsecond: The gray scale coding of the depicted transducer is meaningless.

Figure 3:
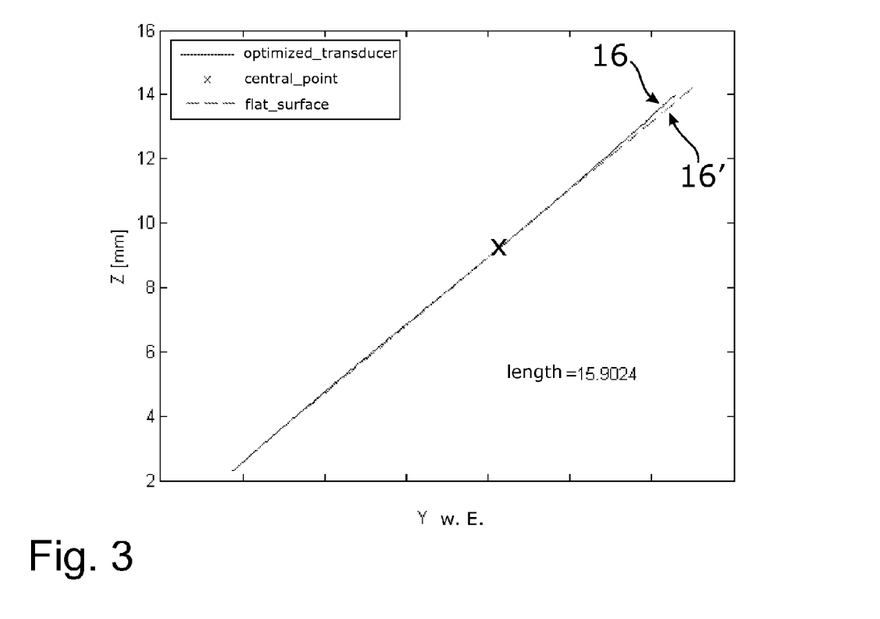
FIG. 3: shows a cut through the transducer surface of the delay line body, at which the ultrasonic transducer is located, in the plane of incidence.

FIG. 3 shows a cut through the transducer surface 16 of the delay line body 12 of a test probe 10 according to the present invention, which is based on a transducer 20 according to FIG. 2, in which the cut was carried out in the intromission plane. The intromission plane is defined by the direction of propagation of the ultrasonic sound in the workpiece and the surface normal on the work-piece surface area 102 in the coupling point of the ultrasonic sound. The broken line in FIG. 3 shows the planar course of the transducer surface 16' usual in the prior art, the continuous line indicates the actual surface course 16. The point denoted by X indicates the exit point of the central beam of the ultrasonic transducer 20. It can be clearly seen, that the point X of the ultrasonic transducer 20 lies on the continuous line, but on both sides of the point X deviations from the planar surface course arise. Thereby, the line standing perpendicular in the point X on the (not-depicted) transducer is the central beam in the delay line body 12 and its direction determines the intromission angle β according to Snellius.

Figure 4:
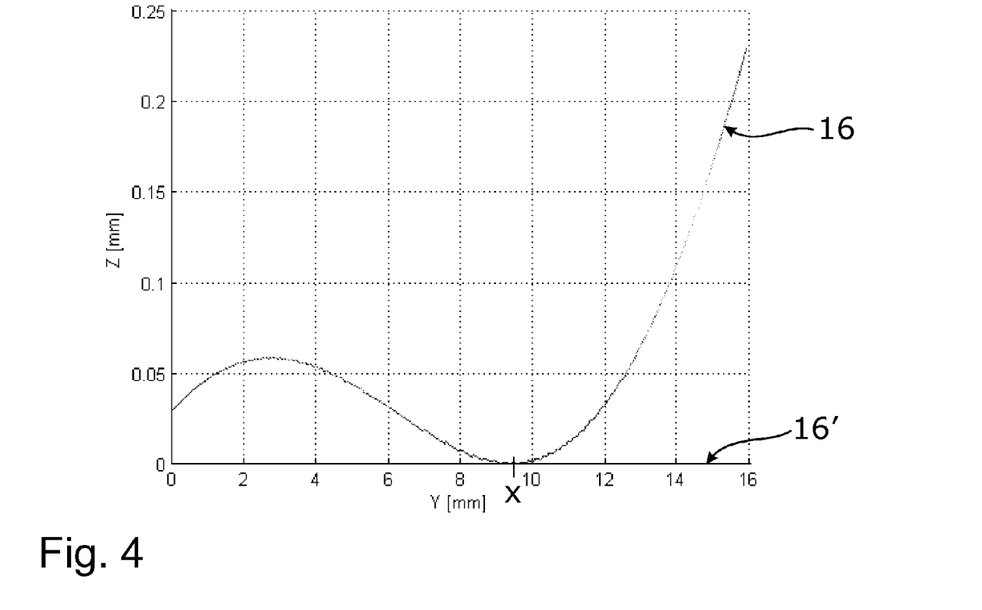
FIG. 4: shows a scaled depiction of the deviation of the intersection line from FIG. 3 from a straight line, which represents a plane transducer surface known from the prior art.

FIG. 4 now shows the cut through the optimized transducer surface 16 of the test probe 10 according to FIG. 3 in the enlarged depiction (after appropriate coordinate transformations), in which the y-axis indicates here the deviation of the calculated transducer form in millimeters from a planar area. As can clearly be seen, the deviations from the planar area lie only in the range of fractions of a millimeter. Furthermore, it can be seen, that based on the idealized plane transducer surface 16', the optimized surface course of the transducer surface 16 can be described as S-shaped, i.e., the cutting line depicted in FIG. 3, based on the planar transducer surface 16' includes a local maximum, a local minimum and a turning point lying in between. Such a design of the transducer surface 16 of the delay line body 12 can be realized, for example, in a mechanical manner in the production of the delay line body 12.

Figure 5:
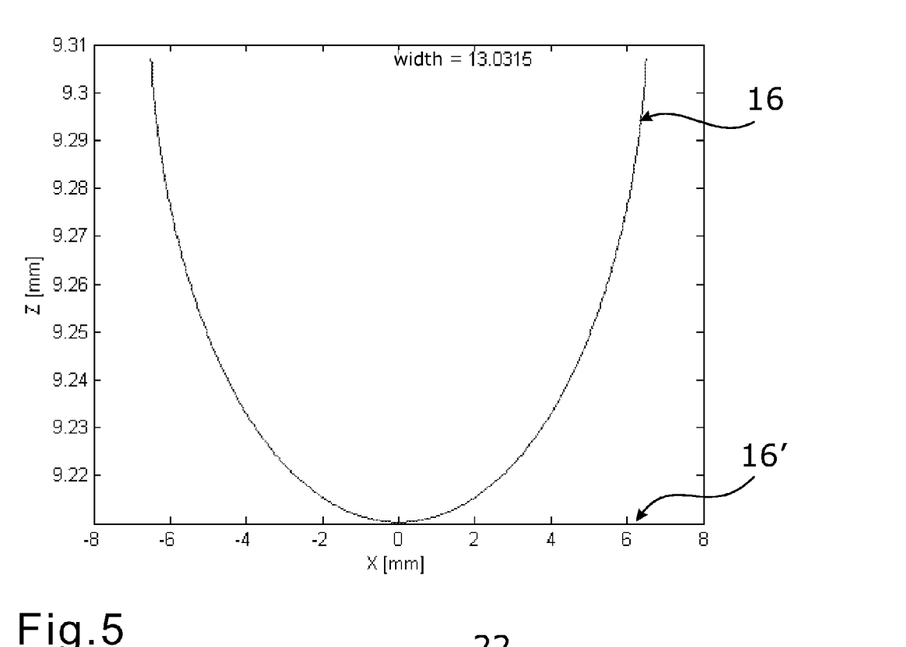
FIG. 5 shows a cut through this area perpendicular to the plane of incidence.

FIG. 5 now shows a cut through the optimized transducer surface 16 of the test probe 10 according to the previously discussed execution example in a direction perpendicular to the plane of incidence, carried out in the already previously defined point X of the ultrasonic transducer 20. The parabolic course of the surface contour in this cut can clearly be seen, in which the deviations from the planar area lie in turn only in the range of fractions of a millimeter, but lead to a defocused sound beam.

Figure 6:
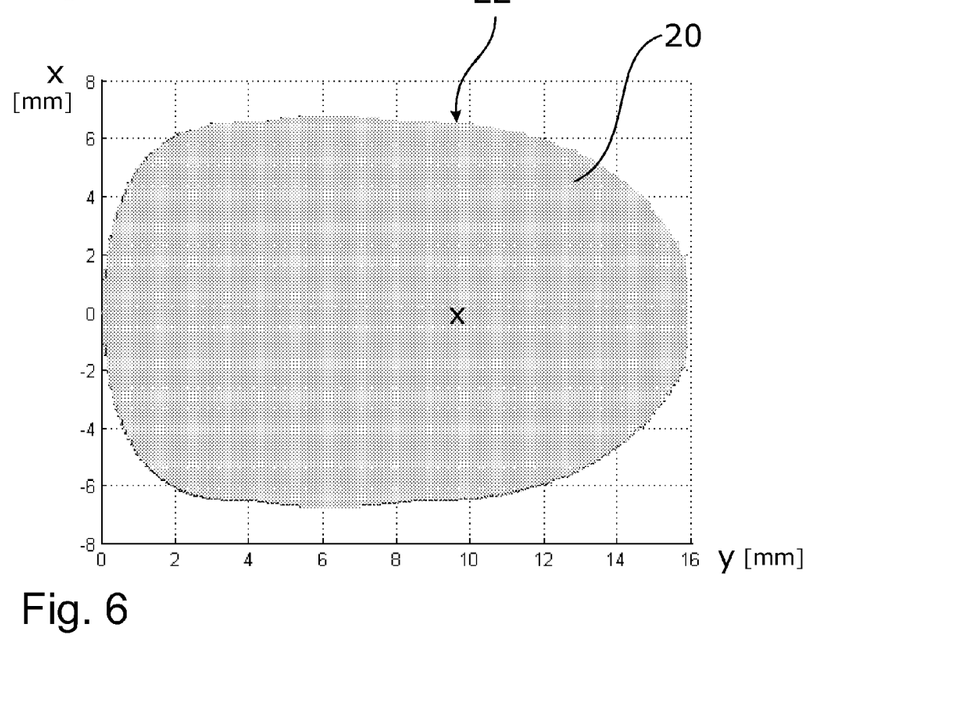
FIG. 6: shows a two-dimensional depiction of an ultrasonic transducer of a test probe according to the present invention, from which the deviation of the circumferential line of the ultrasonic transducer from the hitherto accepted circular or rectangular configuration become clear.

FIG. 6 shows a scaled view of the ultrasonic transducer 20 optimized according to the present invention in FIG. 2, in which the view occurs perpendicular to the optimized transducer surface 16 in the point X.

Figures 7, 8:
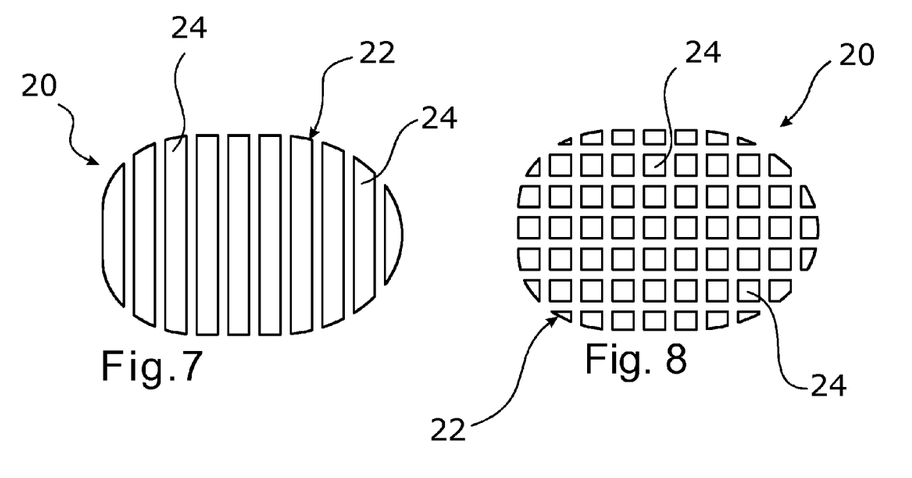
FIG. 7: shows a view of the ultrasonic transducer of a test probe according to the present invention in accordance with a second execution example.
FIG. 8: shows a view of the ultrasonic transducer of a test probe according to the present invention of a third execution example.

As was already elucidated in the introductory part, the ultrasonic transducer 20 can be designed as a individual oscillator. However, it can also be designed in a segmented manner in the form of a linear array, in which the ultrasonic transducer 20 is subdivided into a multitude of individual oscillators 24, which have, for example, the same width. Such a linear array can be learned from FIG. 7. Furthermore, it is possible to design the ultrasonic transducer 20 as a two-dimensional array, as this is shown in an exemplary manner in FIG. 8 for segments essentially of the same width.

Figure 9:
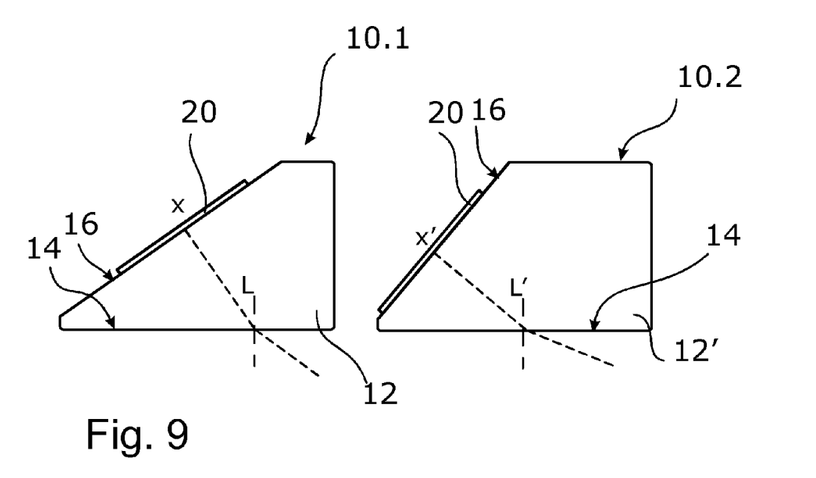
FIG. 9: shows two exemplary test probes of a family of test probes according to the present invention.

Finally, FIG. 9 shows schematically a pair of test probes 10 according to the present invention, in which in the case of the first test probe 10.1 it is a matter of an angular test probe, which is optimized for a fixed intromission angle β=45° and in which the ultrasonic transducer 20 is designed in one-piece. In the case of the second test probe 10.2, it is a matter also of a test probe or the angular intromission of sound, but this time for a fixed intromission angle β'=60°. The test probes 10.1 and 10.2 are thereby adjusted to each other, so that the ultrasonic fields generated by them in each case in the workpiece are essentially in agreement at least in the near field and thereby are preferably rotationally symmetrical to their respective main direction of propagation. An especially simple manageability of the family of test probes results, since the sound paths in the material up to the end of the near field are essentially equal in both test probes 10.1 and 10.2. The points denoted by X indicate that point, at which the central beam cuts the respective transducer 20, 20'.

The invention claimed is:

1. Test probe for the non-destructive testing of a workpiece by means of ultrasonic sound, wherein the test probe is provided for an angular intromission of sound into the workpiece, with an ultrasonic transducer for generation of an ultrasonic field, which is coupled acoustically to a delay line body, which is provided to be attached for a coupling of the ultrasonic field into the workpiece on a surface area of the workpiece, wherein
   a. the ultrasonic field generated by the test probe after the coupling into the workpiece is essentially rotationally symmetrical to a central beam, and
   b. a surface area of the delay line body, at which the ultrasonic transducer is located, is not planar.

2. Test probe according to claim 1, wherein a coupling surface area of the delay line body is curved.

3. Test probe according to claim 1, wherein a circumferential line of the ultrasonic transducer has no rotational symmetry, and is not circular or a regular polygon.

4. Test probe according to claim 1, wherein a design of the surface area of the delay line body, at which the ultrasonic transducer is located, is selected so that a point lying in a main direction of propagation exists, on which a run-time difference between the central beam and perimeter beams amounts to T/2, in which T is a cycle duration of the ultrasonic sound.

5. Test probe (10) according to claim 1, characterized in that the surface area of the delay line body (12), at which the ultrasonic transducer (20) is located, has a nonlinear contour in the intromission plane and in particular has a S-shaped contour.

6. Test probe according to claim 1, wherein the surface area of the delay line body, at which the ultrasonic transducer is located, is described perpendicular to an intromission plane by a function, which has an absolute minimum.

7. Test probe according to claim 6, wherein the function essentially corresponds to a parabola opened upwards.

8. Test probe according to claim 1, wherein the ultrasonic transducer has a majority of independently controllable individual oscillators.

9. Test probe according to claim 8, wherein a rotational symmetry of a sound field exists, if the individual oscillators are controlled in-phase.

10. Test probe according to claim 1, wherein a coupling surface area of the delay line body is planar.

11. Test probe according to claim 1, wherein a coupling surface area of the delay line body is not planar.

12. Family of test probes according to claim 1 whose members are provided for an intromission of sound under several different intromission angles, wherein an end of a near field of all test probes in the workpiece relative to their central beam are essentially in agreement with the ultrasonic field generated by the other test probes relative to their central beam.

13. Family of test probes according to claim 12, wherein a length of sound paths up to the end of the near field in a test material in a direction of the central beam are essentially in agreement in all test probes of the family.

14. Testing device for non-destructive testing of a workpiece by means of ultrasonic sound, comprising:
   a. a test probe, which has an ultrasonic transducer for generation of an ultrasonic field, which
      i. is coupled acoustically to a delay line body, which is provided to be attached to a coupling of an ultrasonic field into the workpiece on a surface of the workpiece, and
      ii. has a majority of independently controllable individual oscillators,
   b. a control unit, which is equipped to control the individual oscillators of the ultrasonic transducer with phase accuracy in such a way, that the ultrasonic field generated by the test probe is angularly introduced into the workpiece and is essentially rotationally symmetrical to its central beam after the coupling into the workpiece.

15. Testing device according to claim 14, wherein the control unit is furthermore equipped to control the individual oscillators of the ultrasonic transducer with phase accuracy in such a way, that a main direction of propagation of the ultrasonic field generated by the test probe can be varied.

16. Testing device according to claim 14, wherein the coupling surface area of the delay line body is not planar.

17. Testing device according to claim 14, wherein the individual oscillators of the ultrasonic transducer are arranged in a form of a two-dimensional array.

18. Test device according to claim 14, wherein the surface of the delay line body, at which the ultrasonic transducer is located, is planar.

19. Testing device according to claim 14, wherein the individual oscillators of the ultrasonic transducer are arranged in a form of a linear array.

20. Testing device according to claim 19, wherein a longitudinal axis of the linear array lies in an intromission plane.

* * * * *

UNITED STATES PATENT AND TRADEMARK OFFICE
CERTIFICATE OF CORRECTION

PATENT NO. : 8,955,384 B2
APPLICATION NO. : 13/319615
DATED : February 17, 2015
INVENTOR(S) : Kleinert et al.

It is certified that error appears in the above-identified patent and that said Letters Patent is hereby corrected as shown below:

Specification

In Column 3, Line 17, delete "rotationallty" and insert -- rotationally --, therefor.

In Column 7, Line 65, delete "and) 70°." and insert -- and 70°). --, therefor.

In Column 9, Line 8, delete "consist of a" and insert -- comprise a --, therefor.

In Column 9, Line 51, delete "mm/microsecond:" and insert -- mm/microsecond. --, therefor.

Claims

In Column 10, Line 66, in Claim 1, delete "with an" and insert -- with a single element --, therefor.

In Column 11, Lines 20-21, in Claim 5, delete "probe (10) according to claim 1, characterized in that the surface" and insert -- probe according to claim 1, wherein the surface --, therefor.

In Column 11, Line 21, in Claim 5, delete "body (12)," and insert -- body, --, therefor.

In Column 11, Line 22, in Claim 5, delete "transducer (20)" and insert -- transducer --, therefor.

In Column 11, Line 23, in Claim 5, delete "the intromission plane and in particular" and insert -- an intromission plane and --, therefor.

In Column 11, Line 41, in Claim 12, delete "Family of test" and insert -- Test --, therefor.

In Column 12, Line 4, in Claim 13, delete "Family of test" and insert -- Test --, therefor.

In Column 12, Line 35, in Claim 18, delete "Test" and insert -- Testing --, therefor.

Signed and Sealed this
Twenty-seventh Day of October, 2015

Michelle K. Lee
*Director of the United States Patent and Trademark Office*